United States Patent
Duong et al.

(10) Patent No.: US 11,103,845 B2
(45) Date of Patent: Aug. 31, 2021

(54) POLYSACCHARIDE AEROGEL

(71) Applicant: NATIONAL UNIVERSITY OF SINGAPORE, Singapore (SG)

(72) Inventors: Hai Minh Duong, Singapore (SG); Nhan Phan-Thien, Singapore (SG); Bowen Gu, Singapore (SG); Mark Pyne Pennefather, Singapore (SG); Thanh Xuan Nguyen, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 16/463,232

(22) PCT Filed: Dec. 7, 2017

(86) PCT No.: PCT/SG2017/050604
§ 371 (c)(1),
(2) Date: May 22, 2019

(87) PCT Pub. No.: WO2018/106190
PCT Pub. Date: Jun. 14, 2018

(65) Prior Publication Data
US 2019/0282988 A1 Sep. 19, 2019

Related U.S. Application Data

(60) Provisional application No. 62/432,244, filed on Dec. 9, 2016.

(51) Int. Cl.
| | | |
|---|---|---|
| *B01J 13/00* | (2006.01) | |
| *C08J 9/28* | (2006.01) | |
| *C08L 1/02* | (2006.01) | |
| *C08L 5/08* | (2006.01) | |
| *A61L 15/22* | (2006.01) | |
| *C08K 3/30* | (2006.01) | |
| *B01D 17/02* | (2006.01) | |
| *C08B 15/00* | (2006.01) | |
| *A61L 24/00* | (2006.01) | |

(52) U.S. Cl.
CPC ......... *B01J 13/0091* (2013.01); *A61L 15/225* (2013.01); *B01D 17/0202* (2013.01); *C08B 15/005* (2013.01); *C08J 9/28* (2013.01); *C08K 3/30* (2013.01); *C08L 1/02* (2013.01); *C08L 5/08* (2013.01); *A61L 24/00* (2013.01); *B01D 17/02* (2013.01); *C08J 2201/026* (2013.01); *C08J 2201/0484* (2013.01); *C08J 2205/026* (2013.01); *C08J 2301/02* (2013.01); *C08J 2405/08* (2013.01); *C08K 2003/3045* (2013.01)

(58) Field of Classification Search
CPC ........ C08J 2205/026; C08J 2301/00–06; B01J 13/0091; C08L 1/00–06
See application file for complete search history.

(56) References Cited

U.S. PATENT DOCUMENTS

| | | | | |
|---|---|---|---|---|
| 2007/0259979 A1* | 11/2007 | Lee | ............ | C08J 9/0085 |
| | | | | 521/64 |
| 2016/0137503 A1* | 5/2016 | Zhang | ............ | B01J 20/3071 |
| | | | | 210/692 |

FOREIGN PATENT DOCUMENTS

| | | |
|---|---|---|
| CN | 102786642 | 11/2012 |
| CN | 103131039 | 6/2013 |
| CN | 105754133 A * | 7/2016 |
| WO | WO 2012/032514 A1 | 3/2012 |
| WO | WO 2014/178797 A1 | 11/2014 |

OTHER PUBLICATIONS

Chen, W. et al. Comparative Study of Aerogels Obtained from Differently Prepared Nanocellulose Fibers. ChemSusChem, 2014, 7, 154-161. First published Jan. 13, 2014. (Year: 2014).*
Machine Translation of CN105754133A. Jul. 13, 2016. (Year: 2016).*
Deng et al. Aerogels from crosslinked cellulose nano/micro-fibrils and their fast shape recovery property in water. Journal of Materials Chemistry, 2012, 22, 11642-11650. (Year: 2012).*
Wan, C. et al. Preparation, Characterization and Oil Adsorption Properties of Cellulose Aerogels from Four Kinds of Plant Materials via a NaOH/PEG Aqueous Solution. Fibers and Polymers, 2015, 16, 302-307. (Year: 2015).*
International Preliminary Report of Patentability for International Application No. PCT/SG20171050604 dated Jun. 11, 2019.
Cheng, et al., "Cotton aerogels and cotton-cellulose aerogels from environmental waste for oil spillage cleanup", Materials & Design, 130:452-458 (2017).
International Search Report for International Application No. PCT/SG2017/050604 dated Mar. 14, 2018.
Written Opinion for International Application No. PCT/SG2017/050604 dated Mar. 14, 2018.

* cited by examiner

*Primary Examiner* — Stephen E Rieth
(74) *Attorney, Agent, or Firm* — McDonnell Boehnen Hulbert & Berghoff LLP

(57) ABSTRACT

Disclosed herein is a polysaccharide aerogel comprising cotton cellulose fibres and a method of preparing the polysaccharide aerogel. The method comprises: mixing cotton cellulose fibres and a cross-linker to form a mixture; sonicating the mixture; freezing the sonicated mixture; and freeze drying the frozen mixture to form an aerogel. A further embodiment provides a polysaccharide aerogel comprising cotton cellulose fibres and paper cellulose fibres in a weight ratio of 1:1 to 1:6 and a method of preparation thereof wherein in the mixing step, the paper cellulose fibres are added to the cotton cellulose fibres to form a mixture.

12 Claims, 9 Drawing Sheets

POLYSACCHARIDE AEROGEL

This application is a U.S. National Phase application under 35 U.S.C. § 371 of PCT/SG2017/050604, filed Dec. 7, 2017, which claims the benefit of U.S. Provisional Application Ser. No. 62/432,244, filed Dec. 9, 2016. The entire disclosure contents of these applications are herewith incorporated by reference in their entirety into the present application.

TECHNICAL FIELD

The present invention relates to a polysaccharide aerogel and a method of forming the same.

BACKGROUND

Haemorrhage control devices are widely used to stop bleeding in the military and civilian first responder sectors. Haemorrhage injuries include two main types: (i) compressible bleeding wounds such as external capillary, venous, arterial bleeding; and (ii) non-compressible wounds such as sub-dermal or internal venous and arterial bleeding. The most commonly used method to stop bleeding is through covering the wound with a bandage, then by applying direct pressure, facilitating the formation of a blood clot. Unfortunately, these wound dressings are often too stiff and rigid to fit into the small and narrow cavity of the casualty. Also, they do not conform to the irregular tissue morphologies of the wound. Another method to facilitate the clotting of wound would be using granular and powder-based haemostatic products, as they are able to conform to irregular tissue morphologies of the wound cavity. However, the significant drawback of these products is that they can only be deployed in calm conditions.

Existing haemorrhage control products include QuickClot Combat Gauze and XSTAT 30 from RevMedx. The XSTAT 30 devices can deliver the compressive forces within the wound cavity while common haemorrhage control techniques can only apply the compression externally. The XSTAT devices comprise of a syringe filled with little capsules of sponges. The syringe is inserted into the bullet wound of a casualty. The cellulose-based sponges are then injected into the wound where they expand quickly and absorb the blood. With the fast expansion of the capsules, a haemostatic pressure created causes to stop blood flow within the wound. However, the XSTAT devices still have some limitations. For example, the expansion rate of the cellulose-based sponges is slow and they only achieve full length after 15 seconds of expansion. Further, the cellulose based sponges made from wood pulp may not absorb the blood very fast. These make the XSTAT devices ineffective for deep penetration into an irregular wound cavity.

With the unsuitability of the different bleeding control methods currently in the art, there is therefore a need for an improved haemorrhage control device.

SUMMARY OF THE INVENTION

The present invention seeks to address these problems, and/or to provide an improved device for use as a haemorrhage control device.

In general terms, the invention relates to an aerogel which is mechanically robust, fast expanding and highly hydrophobic. The aerogel may be used for several applications, including as a haemorrhage control device or in oil absorption. Used as a haemorrhage control device, the aerogel may be safely administered for human medical treatment. The highly absorptive aerogel may be compressed and injected into a bleeding wound. The aerogel may counter the systolic blood pressure within the wound cavity, thereby stopping further loss of blood. The aerogel may also promote blood clotting and tissue healing through the use of additives, and removal of excess blood accumulated in the wound cavity. Accordingly, the aerogel may create a temporary physical barrier to blood flow, which could allow time for the patient on which the aerogel is used to receive surgical care.

According to a first aspect, the present invention provides a polysaccharide aerogel comprising cotton cellulose fibres. In particular, the aerogel may be compressible.

The aerogel may comprise a suitable amount of cotton cellulose fibres. For example, the aerogel may comprise 0.5-1.5 weight % cotton cellulose fibres. In particular, the aerogel may comprise 0.5-1.5 weight %, 0.7-1.2 weight %, 0.8-1.1 weight %, 0.9-1.0 weight % cotton cellulose fibres. Even more in particular, the aerogel may comprise 0.7 weight % cotton cellulose fibres.

The aerogel may further comprise paper cellulose fibres. The aerogel may comprise any suitable amount of paper cellulose fibres for the purposes of the present invention. According to a particular aspect, the aerogel may comprise a suitable amount of cotton cellulose and paper cellulose fibres. For example, the weight ratio of cotton cellulose to paper cellulose fibres comprised in the aerogel may be 1:1 to 1:6. In particular, the cotton cellulose fibres and the paper cellulose fibres may be comprised in the aerogel in a weight ratio of 1:1-1:6, 1:1-1.5, 1:1-1.4, 1:1-1.3, 1:1-1.2. Even more in particular, the weight ratio may be 1:2.

According to a particular aspect, the aerogel may comprise at least one cross-linker. The cross-linker may be any suitable cross-linker. For example, the cross-linker may be a wet-strength resin. In particular, the cross-linker may be polyamide-epichlorohydrin (PAE), such as Kymene 557H.

The aerogel may further comprise at least one additive. The at least one additive may be any suitable additive. For example, the additive may be a radioactive marker, such as barium sulphate. Another example of a suitable additive is chitosan.

The second aspect of the present invention provides a device comprising the aerogel according to the first aspect. The device may be any suitable device such as a haemorrhage control device or an oil absorption device.

According to a third aspect, there is provided a method of forming the polysaccharide aerogel according to the first aspect, the method comprising:
mixing cotton cellulose fibres and a cross-linker to form a mixture;
sonicating the mixture;
freezing the sonicated mixture; and
freeze drying the frozen mixture to form an aerogel.

The mixing, sonicating, freezing and freeze drying may be under suitable conditions.

According to a particular aspect, the mixing may further comprise mixing at least one additive. The at least one additive may be as described above.

The mixing may further comprise mixing paper cellulose fibres. Any suitable amount of paper cellulose fibres may be mixed during the mixing. In particular, the mixing may comprise mixing cotton cellulose fibres and paper cellulose fibres in a weight ratio of 1:1: to 1:6. In particular, the cotton cellulose fibres and the paper cellulose fibres may be mixed in a weight ratio of 1:1-1:6, 1:1-1.5, 1:1-1.4, 1:1-1.3, 1:1-1.2. Even more in particular, the weight ratio may be 1:2.

The method may further comprise compressing the aerogel following the freeze drying.

BRIEF DESCRIPTION OF THE DRAWINGS

In order that the invention may be fully understood and readily put into practical effect there shall now be described by way of non-limitative example only exemplary embodiments, the description being with reference to the accompanying illustrative drawings. In the drawings.

DETAILED DESCRIPTION

Figure 1:
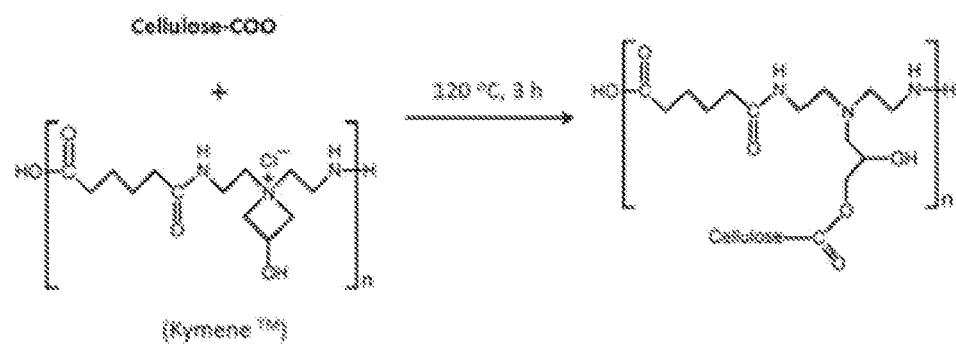
FIG. 1 shows cross-linking formation between cellulose fibres and Kymene™.

The present invention provides a polysaccharide aerogel with improved expansion speed and absorption properties, thereby making the aerogel useful in several applications such as for use in haemorrhage control, heat insulation, water or oil absorption.

The aerogel according to the present invention provides several advantages. For example, when used in a haemorrhage control device, the aerogel, being highly hydrophilic, is able to absorb and remove large volumes of excess blood in wound cavity due to the existence of large number of pores in the aerogel, which acts as fluid storage compartments within the material. Further, as the aerogel comprises cotton cellulose fibres which are hydrophilic, the aerogel is able to retain water with high stability. At the same time, since the aerogel comprises cellulose fibres, the aerogel is biocompatible and biodegradable. The cost of making the aerogel is also reduced in view of the materials required to make the aerogel being cheap and available in abundance. Another advantage of the aerogel is that the aerogel according to the present invention is compressible. Accordingly, in use, the aerogels may be able to expand and exert pressure on a wound on which the aerogel is used, making it particularly useful for haemostatic treatment.

According to a first aspect, the present invention provides a polysaccharide aerogel comprising cotton cellulose fibres. For the purposes of the present invention, an aerogel is defined as a low-density and highly porous solid structure in which the liquid component is replaced by a gas. In particular, the polysaccharide aerogel comprises a random network of cotton cellulose fibres of short lengths which forms a fibrous structure that provides mechanical integrity to the aerogel.

The aerogel may comprise a suitable amount of cotton cellulose fibres. For example, the aerogel may comprise 0.5-1.5 weight % cotton cellulose fibres. In particular, the aerogel may comprise 0.5-1.5 weight %, 0.7-1.2 weight %, 0.8-1.1 weight %, 0.9-1.0 weight % cotton cellulose fibres. Even more in particular, the aerogel may comprise 0.7 weight % cotton cellulose fibres. The weight % is the initial concentration of the cotton cellulose fibres in cotton solution with water used in the preparation of a hydrogel. Accordingly, 0.7 weight % indicates the amount of dried cotton cellulose fibres in 100 ml of water or approximately 100 g of water.

The cotton cellulose fibres may be of any suitable cotton. In particular, the cotton may be any suitable cellulose-based material having both amorphous and semi-crystalline structures. For example, the cotton cellulose fibres may be of, but not limited to, *Gossypium hirsutum*, *Gossypium barbadense*, *Gossypium arboreum*, *Gossypium herbaceum*, or a combination thereof.

In particular, the aerogel may be compressible. According to a particular aspect, the aerogel may be compressed into a pellet or a packed structure by application of a mechanical force. For the purposes of the present invention, compressible is defined as the aerogel's ability to recover its original shape quickly after compression-release without damaging its structure.

The aerogel may further comprise paper cellulose fibres. Accordingly, the aerogel may comprise a mixture of cotton cellulose and paper cellulose fibres. The aerogel may comprise a suitable amount of cotton cellulose fibres and paper cellulose fibres. According to a particular aspect, the weight ratio of cotton cellulose fibres to paper cellulose fibres comprised in the aerogel may be 1:1 to 1:6. In particular, the cotton cellulose fibres and the paper cellulose fibres may be comprised in the aerogel in a weight ratio of 1:1-1:6, 1:1-1:5, 1:1-1.4, 1:1-1.3, 1:1-1.2. Even more in particular, the weight ratio may be 1:2.

The paper cellulose fibres may be from any suitable source. For example, the paper cellulose fibres may be extracted from a recyclable material such as, but not limited to, waste paper, such as high-grade paper for example, computer paper, white paper, tab cards, and the like, as well as other types of paper for example, coloured paper, corrugated cardboards, newspapers, magazines, telephone books, catalogues, envelopes, wrapping papers, packing papers, paper bags, and the like.

The cotton cellulose fibres may be longer and thicker compared to the paper cellulose fibres. Accordingly, the cotton cellulose fibres serve as a scaffold to provide strength and mechanical stability, while the paper cellulose fibres improve the aerogel's effectiveness in absorbing fluids.

According to a particular aspect, the aerogel may comprise at least one cross-linker. The cross-linker comprised in the aerogel enables the cross-linking between cotton cellulose fibres.

The cross-linker may be any suitable cross-linker. For example, the cross-linker may be a wet-strength resin. In particular, the cross-linker may be urea-formaldehyde (UF), melamine-formaldehyde (MF) and polyamide-epichlorohydrin (PAE). Even more in particular, the cross-linker may be PAE such as Kymene 557H. Kymene is made of quaternary ammonium groups which form ester bonds between cotton cellulose fibres as the aerogel is dried and cured. In particular, the ester bonding between the azetidinium groups and cellulose carboxyl groups give rise to the cross-linking effect. The ester bonding may enhance the strength of the cotton cellulose fibres and therefore increases structural integrity of the aerogel and in a more flexible aerogel structure. FIG. 1 shows the cross-linking formation between the cotton cellulose fibres and Kymene.

The aerogel may further comprise at least one additive. The at least one additive may be any suitable additive. For example, the additive may be a radioactive marker, such as barium sulphate. The addition of a radioactive marker may be advantageous as it enables the additive, and therefore the aerogel, to be radio opaque and detectable under X-ray scanners. In particular, when the aerogel is used in haemostatic treatment, the aerogel may be visible and therefore may be removed completely from a patient.

Another example of a suitable additive is chitosan. Chitosan is comprised of D-glucosamine and N-acetyl-D-glucosamine randomly distributed along its polymer chains. It also contains a large number of hydroxyl groups. Biodegradable and biocompatible chitosan can be derived from the chitin shells of shrimps and other crustaceans with the aid of alkaline substance like sodium hydroxide. In particular, chitosan can accelerate blood clotting, which reduces blood loss and chance of shock or death. It is hypoallergenic and has natural anti-bacterial properties. Chitosan can also reduce pain by blocking the nerve endings of the patient. Accordingly, chitosan may have beneficial medical properties that may improve the effectiveness of the aerogel when used in haemostatic treatment.

The second aspect of the present invention provides a device comprising the aerogel according to the first aspect. The device may be any suitable device such as a haemorrhage control device or an oil or water absorption device. The aerogel of the present invention is able to expand to 8-15 times its volume in a few seconds and has a considerable expansion pressure, thereby making it useful for use in a haemorrhage control device or an oil or water absorption device.

According to a third aspect, there is provided a method of forming the polysaccharide aerogel according to the first aspect, the method comprising:
  mixing cotton cellulose fibres and a cross-linker to form a mixture;
  sonicating the mixture;
  freezing the sonicated mixture; and
  freeze drying the frozen mixture to form an aerogel.

The mixing, sonicating, freezing and freeze drying may be under suitable conditions.

Mixing

The mixing may comprise mixing the cotton cellulose fibres in a suitable solvent, such as deionised water. The cotton cellulose fibres may be as described above. A suitable amount of cotton cellulose fibres may be mixed. For example, the amount of cotton cellulose fibre may be as described above. As mentioned above, the weight % is the initial concentration of the cotton cellulose fibres in cotton solution with the solvent used in the preparation of a hydrogel to form the aerogel.

The cotton cellulose fibres may have an average fibre length of about 3-7 mm. In particular, the cotton cellulose fibres may have an average fibre length of about 5 mm. If the cotton cellulose fibres are of a longer length, the method may further comprise a step of reducing the fibre length of the cotton cellulose fibres prior to the mixing. Any suitable method may be used for reducing the fibre length. For example, the reducing of the fibre length may be by one or more of: mechanical blending, ultra-sonication.

According to a particular aspect, the mixing may further comprise mixing at least one additive. The at least one additive may be as described above. A suitable amount of additive may be mixed. For example, when the additive is a radioactive marker, the amount of additive added may be 0.1-0.5 weight % based on the initial concentration of the additive in the mixture used in the preparation of the hydrogel to form the aerogel. In particular, the additive may be barium sulphate and the amount added may be 0.1 weight %.

The cross-linker may be as described above. A suitable amount of cross-linker may be added in the mixing. For example, the amount of cross-linker added may be 1-3 weight % based on the initial concentration of the additive in the mixture used in the preparation of the hydrogel to form the aerogel. In particular, the cross-linker may be Kymene and the amount added may be 2.5 weight %.

The mixing may further comprise mixing paper cellulose fibres. Any suitable amount of paper cellulose fibres may be mixed during the mixing. In particular, the mixing may comprise mixing cotton cellulose fibres and paper cellulose fibres in a weight ratio of 1:1: to 1:6. In particular, the cotton cellulose fibres and the paper cellulose fibres may be mixed in a weight ratio of 1:1-1:6, 1:1-1.5, 1:1-1.4, 1:1-1.3, 1:1-1.2. Even more in particular, the weight ratio may be 1:2.

The paper cellulose fibres may have an average fibre length of about 0.3-5.0 mm. If the paper cellulose fibres are of a longer length, the method may further comprise a step of reducing the fibre length of the paper cellulose fibres prior to the mixing. Any suitable method may be used for reducing the fibre length. For example, the reducing of the fibre length may be by one or more of: mechanical blending and ultra-sonication.

The mixing may be carried out for a suitable period of time. For example, the period of time for the mixing may be at least 1 hour. In particular, the period of time for the mixing may be 1-48 hours, 5-36 hours, 10-24 hours, 15-20 hours. Even more in particular, the mixing may be for about 24 hours.

The mixing may be carried out at a suitable temperature. For example, the temperature at which the mixing is carried out may be 15-35° C. In particular, the mixing may be carried out at about 18-32° C., 20-30° C., 22-28° C., 25-27° C. Even more in particular, the mixing may be carried out at about 25° C.

The mixing may comprise stirring. In particular, the mixing may comprise stirring on a magnetic stirrer. The magnetic stirrer may be stirring at a suitable speed. According to a particular aspect, the magnetic stirrer may be stirring at 2000-5000 rpm. In particular, the speed may be about 4000 rpm.

Sonicating

The sonicating of the mixture obtained from the mixing may be sonicated under suitable conditions so that the cotton cellulose fibres and, if applicable, the paper cellulose fibres may be dispersed more evenly within the mixture. The sonication may be for a suitable period of time at a pre-determined sonication power and may be repeated for a pre-determined number of cycles.

For example, the sonication may be carried out for at least 5 minutes. In particular, the sonication may be carried out for 5-15 minutes, 7-12 minutes, 8-10 minutes. Even more in particular, the sonication may be carried out for about 10 minutes.

For example, the sonication may be carried out for at least 1 cycle. In particular, the sonication may be carried out for 1-10 cycles, 2-8 cycles, 3-6 cycles, 4-5 cycles. Even more in particular, the sonication may be carried out for 6 cycles.

For example, the sonication may be carried out at a sonication power of at least 200 W. In particular, the sonication may be carried out at a sonication power of 200-600 W, 300-500 W, 350-450 W, 375-400 W. Even more in particular, the sonication may be carried out at about 400 W.

Freezing

The sonicated mixture may be subjected to freezing under suitable conditions. For example, the freezing may be at a suitable temperature and for a pre-determined period of time to enable the solvent, such as water, to solidify.

For example, the freezing may be carried out at −100° C.−−5° C. In particular, the freezing may be carried out at −90° C.−−10° C., −80° C.−−20° C., −70° C.−−30° C., −60° C.−−40° C., −55° C.−−50° C. In particular, the freezing may be carried out at about −12° C.

For example, the freezing may be carried out for at least 2 hours. In particular, the freezing may be carried out for 2-48 hours, 5-40 hours, 10-36 hours, 15-30 hours, 20-28 hours, 24-26 hours. In particular, the freezing may be carried out for about 24 hours.

Freeze Drying

The frozen mixture may be subjected to freeze drying under suitable conditions. For example, the freeze drying may be for a pre-determined period of time to form an aerogel. The freeze drying removes the solvent from the mixture and creates void spaces in the resultant aerogel. Accordingly, the aerogel formed from the method comprises of almost 95-99 weight % air. The freeze drying may be for at least 5 hours. In particular, the freeze drying may be for 5-96 hours, 10-90 hours, 12-84 hours, 15-72 hours, 24-60 hours, 30-48 hours, 35-40 hours. In particular, the freeze drying may be for about 72 hours.

The method may further comprise compressing the aerogel following the freeze drying. The compressing may be by any suitable method. For example, the compressing may be by using a suitably sized syringe to form aerogel pellets.

The weight of the aerogel obtained from the method of the present invention is approximately equal to the total weight of input cellulose fibres and the cross-linker.

The present invention will be exemplified by the following non-limiting examples.

Example 1

In this example, three performance parameters of volume expansion time, expansion ratio and hydrostatic pressure, relevant to application of the aerogel of the present invention as a haemostatic agent are determined. The effects of different compositions of cotton fibres, cellulose fibres and chitosan on the performance of the aerogels are compared with commercial XSTAT devices.

Materials

The recycled paper cellulose fibres were sourced from Insul-Dek Engineering Pte Ltd (Singapore). Kymene 557H wet strength resin was obtained from Ashland (Taiwan). All solutions were produced using deionized water (DI water). Cotton fibres were purchased off-the-shelf from local supermarkets (Singapore). Chitosan powder was sourced from Sigma-Aldrich Chemical Co.

Fabrication of Pure Cotton Aerogels (C1 Aerogels)

The pure cotton aerogels named as the C1 aerogels were produced from commercially available cotton fibres. Initially, the cotton fibres were mechanically blended using Tefal 400 W blender and underwent ultra-sonication treatment to reduce the fibre length. The cotton fibres had a length of between 0.5-5.0 mm and a diameter from 15.45-16.53 μm. 0.5 g of the blended cotton fibres was then added in 100 mL deionised (DI) water at room temperature. Cross-linker Kymene was then added at 2.5 wt % of the dry weight of the blended cotton fibres. The obtained mixture was stirred for 24 hours at 4000 rpm in a mixer to achieve homogeneity. Finally, the slurry was stored under refrigeration at −12° C. for 24 hours for icing the suspension, and then freeze-dried for 72 hours to form the C1 aerogels. The C1 aerogels were cured at 120° C. for another 3 hours to activate the cross-linking of the Kymene and mechanically strengthen the obtained C1 aerogels having 0.5 wt % of the cotton fibres.

The above was repeated to obtain aerogels comprising 0.7 wt % and 1.0 wt % cotton fibres, with the exception that 0.7 g and 1.0 g of blended cotton fibres was added instead of 0.5 g.

Figure 2:
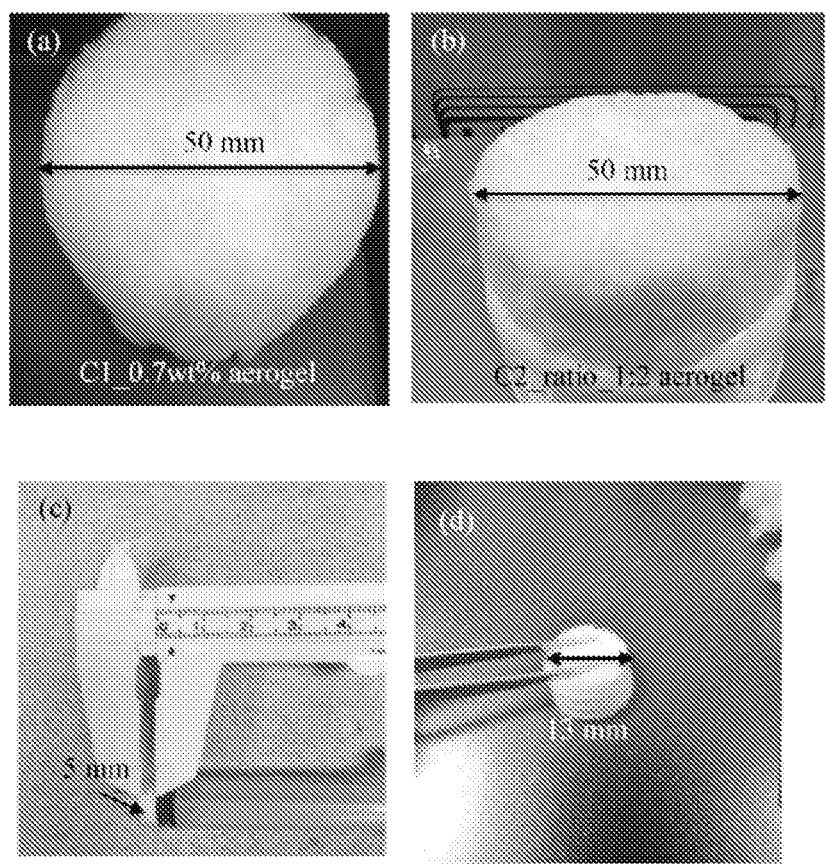
FIG. 2 shows photographs of (a) pure cotton aerogel having 0.7 weight % cotton fibres, (b) paper cellulose-cotton aerogel having 0.7 weight % and a cellulose-cotton ratio of 1:2, (c) aerogel pellet having a height of 5 mm, (d) aerogel pellet having a diameter of 13 mm.

FIG. 2(a) shows the pure cotton aerogels C1 obtained having 0.7 wt % of the cotton fibres.

Fabrication of Cellulose-Cotton Aerogels (C2 Aerogels)

The paper cellulose-cotton aerogels having various paper cellulose-cotton ratios, called C2 aerogels were formed. The recycled paper cellulose fibres had a length of 0.3-5.0 mm and diameter of 13-15 μm. The paper cellulose-cotton ratios were fixed at 1:2, 1:4 and 1:6, respectively. 200 mL of DI water was added to the fibre mixture and they were blended by using Tefal 400 W blender. Kymene (33.3 μL per 100 g water) was then added to the above suspension and went through a probe sonication process (Hielscher Ultrasound Technology) for 5 minutes at 140 W. During the mechanical blending and the sonication, the fibrous mixture achieved macro-scale homogeneity. The obtained fibre slurry was then placed in a refrigerator at −18° C. and then went through freeze-drying at −98° C. for 2-4 days to obtain the C2 aerogels. The C2 aerogels were cured at 120° C. for another 3 hours to cause cross-linking of Kymene and mechanically strengthen the obtained aerogels. FIG. 2(b) shows the cellulose-cotton aerogel C2 having 0.7 wt % of the paper cellulose and cotton fibres and the cellulose-cotton ratio of 1:2.

Fabrication of Chitosan-Coated Cellulose Cotton Aerogels (C3 Aerogels)

The 0.7 wt % cotton-cellulose aerogel having the constant paper cellulose-cotton ratio of 1:2 was chosen to further investigate the effects of different chitosan concentrations on the performance of the chitosan-coated cotton-paper cellulose aerogels, called C3 aerogels. For the fabrication of the C3 aerogel having 0.5 wt % chitosan, the chitosan solution was first prepared. Using a magnetic stirrer, 2.0 g of acetic acid was added to 100 mL of DI water and kept in an ice bath. 1.0 g of the chitosan powder was then slowly added into the dilute acetic acid solution until it became a clear yellowish solution. Next, 0.467 g of cotton fibres and 0.93 g of cellulose fibres were added into 100 mL of DI water. In order to produce a slurry, the solution was sonicated 5 times at 3 minute intervals. The chitosan solution and 2.1 g of Kymene were added into the cellulose-cotton slurry solution using a pipette. The solution was sonicated 5 times at 3 minute intervals and placed in the freezer for 24 hours to form the wet gel.

The above was repeated to obtain aerogels comprising 1.0 wt % and 1.5 wt % chitosan, instead of 0.5 wt %.

To obtain the final C3 aerogels, the wet gel was freeze-dried for 72 hours, and finally cured for 120° C. for 3 hours.

Figure 3:
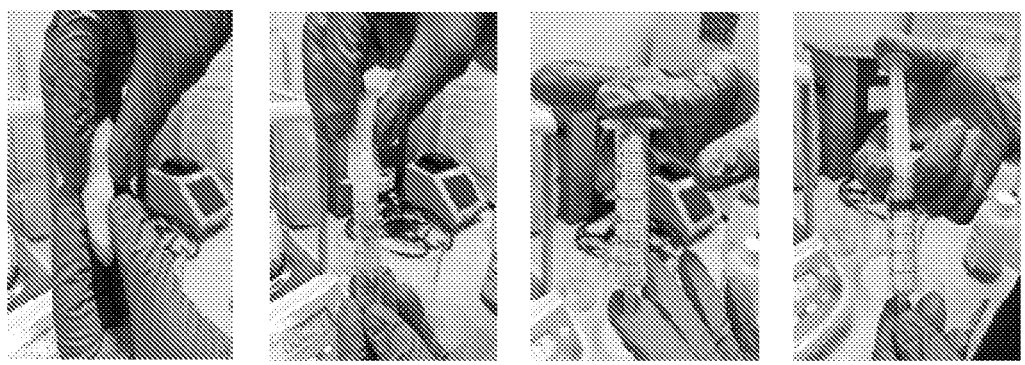
FIG. 3 shows the process of compressing the aerogel according to one embodiment of the present invention into pellets.

Finally, the obtained C1, C2 and C3 aerogels were compressed by using a 15-ml clinical syringe having a diameter of 15 mm to form the aerogel pellets as shown in FIGS. 2(c) and 2(d). FIG. 3 shows how the aerogel is compressed into the pellets.

The characteristics of the compressed C1, C2 and C3 aerogel pellets prepared are summarised in Table 1.

TABLE 1

Summary of C1, C2 and C3 aerogel performance in DI water. The maximum standard deviation of the data is 1.0%.

| Aerogel pellets | Expansion ratio | Expansion time (s) | Hydrostatic Pressure (mmH$_2$O) | Hydrostatic Pressure (mmHg) |
|---|---|---|---|---|
| Pure cotton aerogels (C1 Aerogels) | | | | |
| C1_0.5 wt% | 18.6 | 15.9 | 120 | 8.8 |
| C1_0.7 wt% | 15.7 | 20.8 | 109 | 8.0 |
| C1_1.0 wt% | 15.5 | 21.0 | 104 | 7.7 |
| Pure cotton aerogels (C2 Aerogels) | | | | |
| C2_ratio_1:2 | 14.8 | 7.0 | 98 | 7.2 |
| C2_ratio_1:4 | 10.8 | 8.2 | 94 | 7.0 |
| C2_ratio_1:6 | 10.0 | 11.7 | 92 | 6.8 |
| Chitosan-coated paper cellulose-cotton Aerogels (C3) | | | | |
| C3_chi_0.5 wt % | 16.0 | 4.5 | 155 | 11.5 |
| C3_chi_1.5 wt % | 11.8 | 5.2 | 143 | 10.6 |
| C3_chi_1.5 wt % | 12.2 | 30.0 | 146 | 10.8 |

Characterization

Sample morphology was investigated by a scanning electron microscope (SEM, JSM-6010 of Japan). Before the testing, samples were sputtered with a thin layer gold via JEOL sputter (JFC-1200) at 20 mA for 30 seconds to enhance their electrical conductivity.

Expansion time and volume expansion ratio were measured using the same experiment, but with different measurement methods. For the expansion tests, the aerogel was first compressed to form a pellet having the thickness of 5 mm. It was then placed into a petri-dish filled ⅔ with DI water.

Expansion time was measured from the moment the aerogel contacting the water until it reached full expansion. Full expansion of the aerogel can be observed by the darkening of the aerogel across its entire length due to saturation by water. Full expansion can also be observed by the point where further expansion is insignificant. Expansion ratio was measured by taking the ratio between the fully expanded length and its original compressed length of the aerogel.

Expansion ratio=(Final Length ($L_f$)−Initial Length ($L_i$)/Initial Length ($L_i$)

A U-tube manometer filled with DI water was used to measure the hydrostatic pressure provided by the compressed aerogel pellets. The manometer was first filled to the brim with DI water. The hybrid aerogel was compressed into a syringe using a plunger and the syringe was then attached onto one end of the manometer. A small jet of air was pumped into the other end of the manometer to excite absorption. The final height difference between the ends of the manometer was the hydrostatic pressure provided by the aerogel in mmH$_2$O, which was then converted to mmHg.

Figure 4:
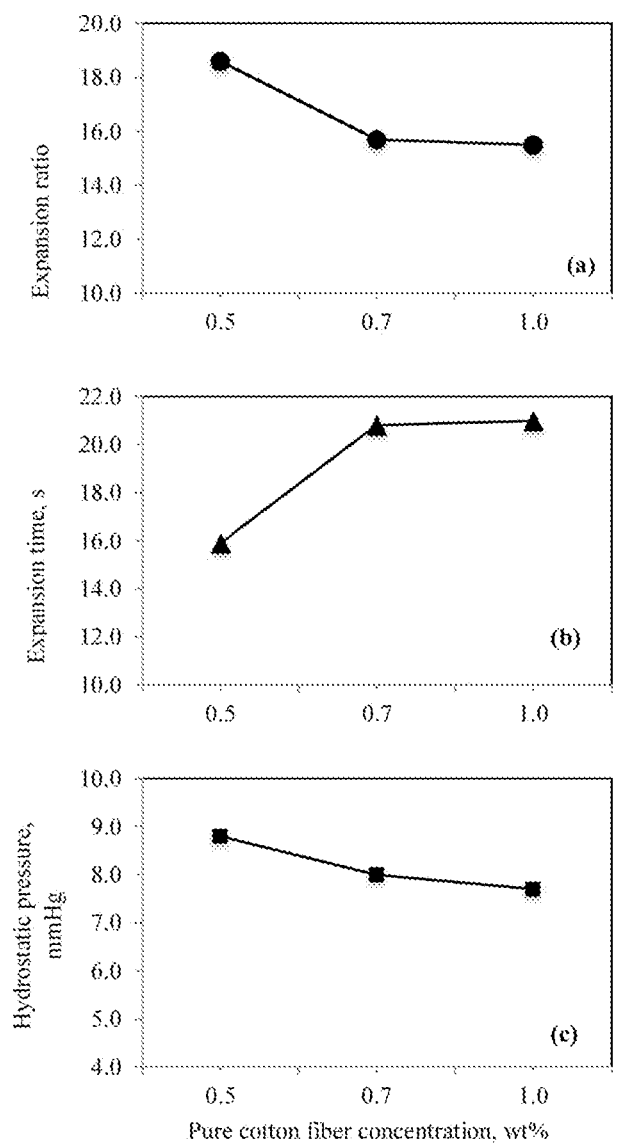
FIG. 4 shows (a) volume-expansion ratio, (b) expansion time and (c) hydrostatic pressure of pure cotton aerogels having different weight % of cotton fibres.
Figure 5:
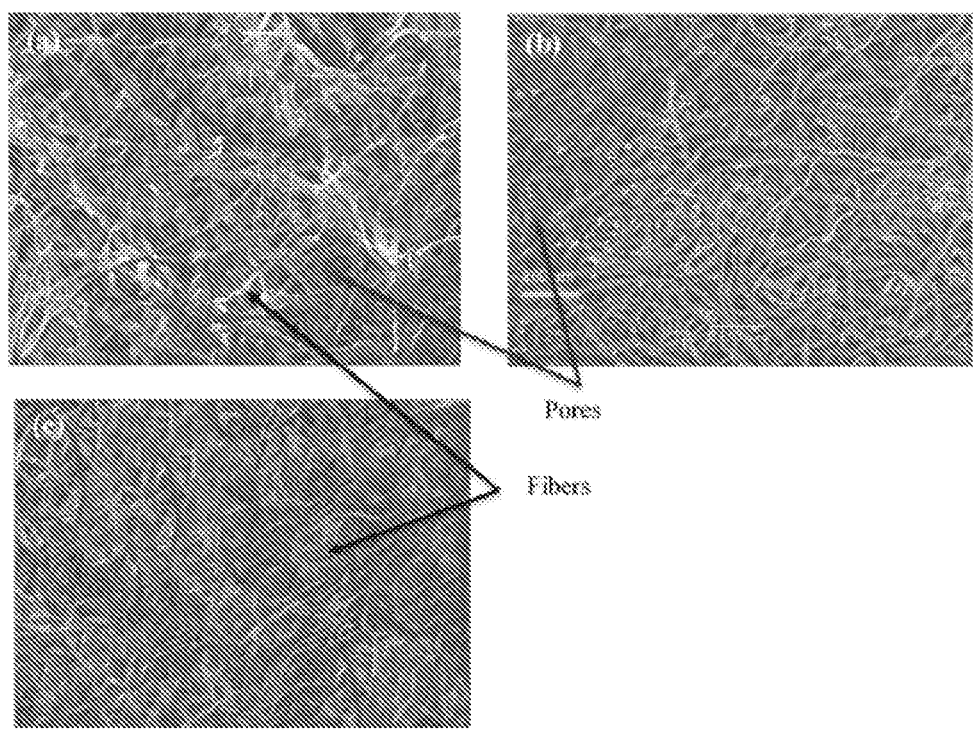
FIG. 5 shows the Field Emission Scanning Electron Microscope (FESEM) images of pure cotton aerogels having (a) 0.5 weight %, (b) 0.7 weight % and (c) 1.0 weight % of cotton fibres.

Results and Discussion (a) Performance of the C1 Aerogels with Different Cotton Fibre Concentrations FIG. 4 compares the volume expansion ratio, expansion time and hydrostatic pressure of the C1 aerogels having the different cotton concentrations. When the cotton fibre concentration of the C1 aerogel pellets increases, their volume expansion ratio and hydrostatic pressure decease. This happens because the C1 aerogel having the larger cotton fibre concentration has a more packed structure as shown in FIGS. 5(a) to (c).

The expansion time of the C1 aerogel pellets having the larger cotton fibre concentration is also larger as more compressed cotton fibres need more time to expand back. Table 1 shows the pure cotton aerogel pellet having 0.5 weight % of the cotton fibres (referred to as the C1_0.5 wt % aerogel pellet) exhibits the largest expansion ratio of 18.56, the fastest expansion time of 15.85 seconds, and the largest hydrostatic pressure of 8.8 mmHg. The expansion performance of the C1_0.5 wt % and C1_0.7 wt % aerogel pellets are very competitive with that of commercial XSTAT sponges. However, for compression process of the aerogel pellets, the C1_0.7 wt % aerogel pellets may be handled more easily nd disintegrate less than the C1_0.5 wt % ones for use as a haemostatic agent. Therefore, the C1_0.7 wt % aerogel pellets were chosen to investigate further properties as discussed below.

(b) Performance of the C2 Aerogels with Different Paper Cellulose-Cotton Ratios

Although the expansion time of the C1-0.7 wt % aerogel pellets was less than 16 seconds, this value may be improved with the addition of cellulose fibrers. While the weight percentage of the fibres in the C2 aerogel pellets was kept constant at 0.7 wt %, the paper cellulose-cotton ratios were varied to 1:2, 1:4 and 1:6. Table 1 shows that addition of cellulose fibres from paper in the C2 aerogel pellets can significantly reduce the expansion time. For example, the paper cellulose-cotton aerogel pellets having the ratio of 1:2, referred to as the "C2_ratio_1:2" aerogel pellets in Table 1, can reduce the expansion time from 20.8 seconds to 7.0 seconds. This happens because the cellulose fibre length and diameter is smaller than the cotton fibre length in the C2 aerogel pellets and therefore the cellulose fibres need less time to expand. Also, the cellulose fibres from paper have an amorphous structure which absorb the water faster than the semi-crystalline structure of the cotton fibres.

Figure 6:
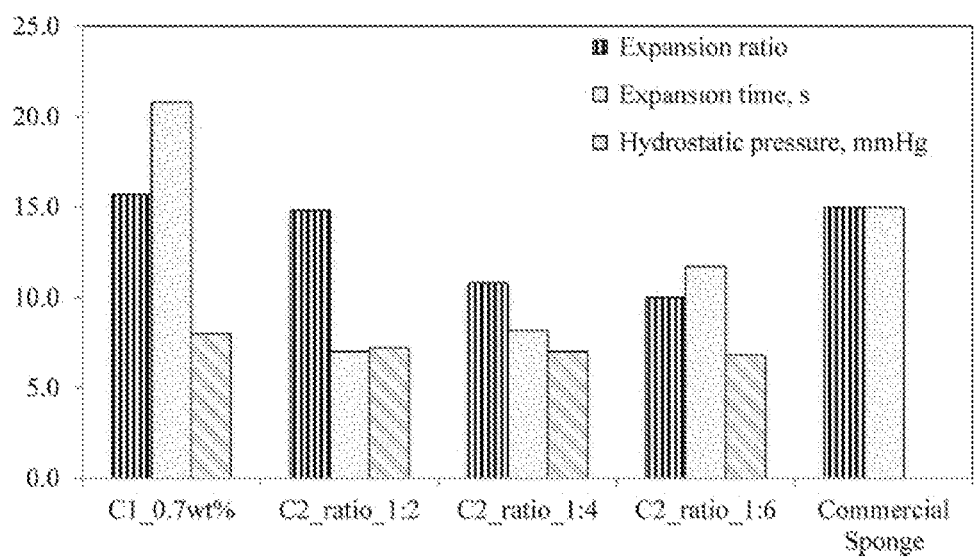
FIG. 6 shows the effect of different paper cellulose-cotton ratios on the haemostatic performance of the aerogel pellets.

Comparing with the C1_0.7 wt % aerogel pellet with no paper cellulose fibres, the C2_ratio_1:2 aerogel pellet in FIG. 6 exhibits three-fold improvement in the expansion time, but its expansion ratio and hydrostatic pressure decrease slightly. Comparing with the 15 second expansion time of XSTAT cellulose-based sponges, it can be seen that all the C2 aerogel pellets expand much faster with expansion times ranging from 7.0-11.7 seconds. The C2 aerogels also exhibit good structural integrity without disintegration. As the C2_ratio_1:2 aerogel pellets show the best performance among the three C2 aerogel pellets investigated in Table 1, these were chosen to further investigate the effects of different chitosan concentrations on their volume expansion ratio, expansion time and hydrostatic pressure.

(c) Performance of the C3 Aerogels with Different Chitosan Concentrations

Figure 7:
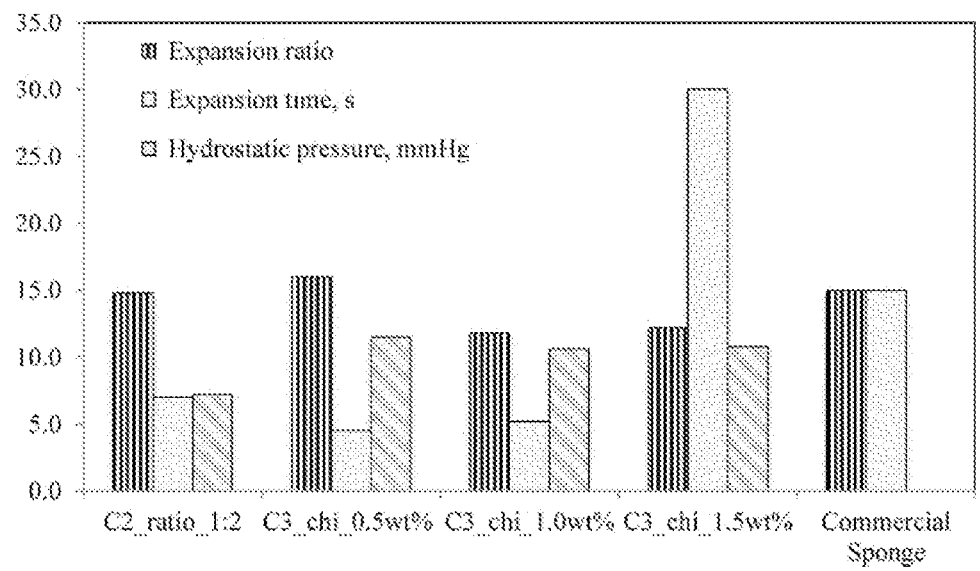
FIG. 7 shows the effect of different chitosan concentrations on the haemostatic performance of the aerogel pellets.

FIG. 7 shows the 0.5 weight % of chitosan added in the C2_ratio_1:2 aerogel pellets can reduce further the expansion time from 7.0 seconds down to 4.5 seconds, increase the expansion ratio up to 16.0 and the hydrostatic pressure up to 11.5 mmHg. This can be explained by chitosan having a large number of hydroxyl groups in its structure which can improve the hydrophilic properties of the C3 aerogel pellets. Comparing these parameters to that of the XSTAT cellulose-based sponges, the C3_chi_0.5 wt % aerogel pellets can reduce the expansion time by three times with a similar expansion ratio. This means that the C3_chi_0.5 wt % aerogel pellets may stop serious liquid leakage like gun wound three times faster than the commercial sponges.

It has been reported that the hydrostatic pressure ranges from 10 to 62 mm Hg in an injured leg. If the hydrostatic pressure requirement to stop a gun wound is assumed to be 21 mmHg, the potential haemostatic devices need only two C3_chi_0.5 wt % aerogel pellets.

(d) Effects of the Aerogel Pellet Number on the Hydrostatic Pressure

Figure 8:
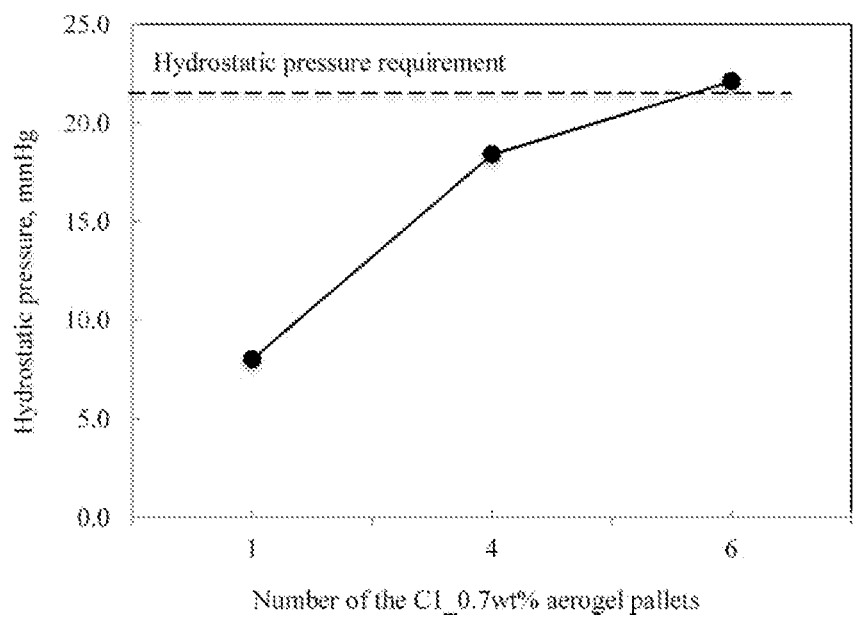
FIG. 8 shows the effects of the 0.7 weight % pure cotton aerogel pellet number on the hydrostatic pressure. The dash line indicates the minimum hydrostatic pressure requirement of the haemostatic requirement.

A number of the C1_0.7 wt % aerogel pellets are placed randomly at the same time in the U-tube manometer filled with DI water to measure the hydrostatic pressure provided by themselves. FIG. 8 shows the effects of the C1_0.7 wt % aerogel pellet number on the hydrostatic pressure. As can be seen in FIG. 8, six C1 cotton aerogel pellets can produce 22.1 mmHg of hydrostatic pressure, which is larger than the minimum hydrostatic pressure requirement (as shown by the dash line in FIG. 8) of the haemostatic requirement. This implies that the haemostatic device using only six C1 aerogel pellets can stop the liquid leakage effectively. The compressed aerogel pellets of the present invention can stop the bleeding much faster and effectively in a few seconds. The cost of the haemostatic device with the same volume using the hybrid cotton aerogel pellets in this work is also much cheaper than that of the XSTAT devices.

(e) Comparison of Morphology

In addition to the above, Brunauer Emmett Teller (BET) experiments were conducted on C1_0.5 wt % and C2_ratio_1:2 aerogels. The results are as shown in Table 2. In summary, the paper cellulose-cotton aerogel had a higher surface area and pore volume than the cotton aerogel, while having a lower average pore size. This signifies that the cotton aerogel has more macro pores and therefore performs poorer in terms of fluid absorption, expansion ratio, rate and pressure. Due to the higher amounts of shorter microfibers in paper cellulose-cotton aerogel, there are a greater number of smaller sized pores.

TABLE 2

Morphology of the cotton and paper cellulose-cotton aerogels

| Parameters | Pure cotton cellulose 0.5 weight % (C1_0.5 wt %) | Paper cellulose-cotton 0.7 weight % (C2_ratio_1:2) |
| --- | --- | --- |
| Surface area (m$^2$/g) | 19.829 | 43.934 |
| Pore volume (cc/g) | 0.011 | 0.023 |
| Pore size average (Å) | 10.85 | 10.35 |

Conclusion

The paper cellulose-cotton (C2) aerogel pellets have better performance in terms of the volume expansion ratio and the hydrostatic pressure compared to the pure cotton (C1) aerogel pellets. Changing the ratio of the composition (i.e. cotton fibre:cellulose fibre content) can significantly affect the performance of the C2 aerogel pellets. In particular, the C3 aerogel pellets may be used as the haemostatic agents and show much improvement over XSTAT cellulose-based sponges, especially in terms of the volume expansion time, with a reduction from 15 seconds to less than 5 seconds, even while retaining the structural integrity of the C3 aerogel pellets.

While both pure cotton aerogel and paper cellulose-cotton aerogel have similar structures, the cotton aerogel has relatively larger pore sizes. The larger pores are slower in drawing water into the aerogel porous structure via capillary action. The paper cellulose-cotton aerogels are more effective in absorbing water and expansion due to smaller pores in its structure. Although not mesopores, the pores are more effective in absorbing and storing water and fluids. The paper cellulose-cotton aerogel is also more densely packed due to the higher weight percentage of cellulose content.

Example 2

The aerogel of the present invention was tested for use as an oil absorbent.

Materials

Recycled cellulose fibers from waste paper and polyamide-epichlorohydrin (PAE, Kymene 557H) were obtained from Insul-Dek Engineering Pte. Ltd. (Singapore) and Ashland (Taiwan), respectively. The cotton pads consisting of cotton fibres were purchased from Fairprice Supermarket (Singapore). Motor oil (5w40) and Singer machine oil were purchased from commercial market. Analytical grade methyltrimethoxysilane (MTMS), ethanol, acetone, hexane and dichloromethane were obtained from the Sigma-Aldrich (Singapore). All chemicals were used without further purification.

Synthesis of Pure-Cotton (PC) and Cotton-Paper Cellulose (CC) Aerogels

The cotton pads were cut into small strands (0.5×4 cm) and then were mixed with the paper cellulose fibres recycled from the paper waste in 200 ml deionized water. The cotton-to-cellulose mass ratios were fixed at 1:0 (pure cotton), 1:1, 1:2 and 1:4 and the fibre-to-water mass concentration in the aqueous dispersion was controlled as 0.25 weight %, 0.5 weight % and 0.75 weight %, respectively. Then, the mixture dispersion was homogenized using a juice blender (Tefal 400 W) for 15 minutes. Afterwards, 66.6 μL PAE solution was added into the dispersion, which later went through a sonication process (Hielscher Ultrasound Technology) at 140 W for 5 minutes. The homogenized dispersion was frozen at −18° C. for 24 hours and then dried in vacuum at −98° C. for 96 hours to obtain the monolith aerogels. During the freezing, both cotton and paper cellulose fibres were squeezed due to the volume expansion from water to ice. Finally, these aerogels were cured at 120° C. for another 3 hours.

Hydrophobic Functionalization of the Aerogels

In order to obtain the hydrophobic aerogels for oil absorption, the obtained aerogels were placed in a glass chamber with four polytetrafluoroethylene vials with each containing 1.5 ml MTMS and heated at 70° C. for 12 hours to undergo a silanization process. The silanization process was carried out based on the reaction between hydroxyl groups and alkoxy groups in MTMS. The PC aerogels were prepared using the same method without the addition of the cellulose fibres. The PC aerogels with different fibre-to-water concentrations and the CC aerogels with different cotton-to-cellulose mass ratios are summarized in Table 3, where the parameters changed are marked with bold font.

TABLE 3

Properties of pure cotton (PC) and cotton-paper cellulose (CC) aerogels with different cotton concentrations and cotton-paper cellulose mass ratios.

| Aerogels | Concentration (weight %) | Mass ratios of cotton-paper cellulose | Density (mg cm$^{-3}$) | Porosity (%) |
|---|---|---|---|---|
| PC25 | 0.25 | 1:0 | 5.13 ± 0.29 | 99.66 |
| PC50 | 0.50 | 1:0 | 6.85 ± 0.33 | 99.54 |
| PC75 | 0.75 | 1:0 | 8.22 ± 0.49 | 99.45 |
| CC1-1 | 0.50 | 1:1 | 8.50 ± 0.33 | 99.43 |
| CC1-2 | 0.50 | 1:2 | 6.40 ± 0.08 | 99.57 |
| CC1-4 | 0.50 | 1:4 | 6.19 ± 0.33 | 99.59 |

Characterizations

Sample morphologies were investigated by a scanning electron microscope (SEM, JSM-6010 of Japan). Before the testing, samples were sputtered with a thin layer gold via JEOL sputter (JFC-1200) at 20 mA for 30 seconds to enhance their electrical conductivity.

Sample weight was measured by a digital microbalance with accuracy of 0.01 mg. Water contact angles measurements were carried using a syringe system (VCA Optima goniometer, AST Products Inc. USA) with each droplet of 0.5 μL. The bulk density of the samples was obtained by measuring the mass and volume of the cylinder-shaped aerogels. The porosity, $\phi$, can be calculated by:

$$\phi = 100\left(1 - \frac{\rho_a}{\rho_c}\right) \quad \text{Equation (1)}$$

where $\rho_a$ is the density of the aerogel and $\rho_c$ (1.5 g cm$^{-3}$) is the density for both paper cellulose and cotton fibres since they process similar density.

Equilibrium oil and water absorption tests were also conducted. Each sample (~10 mg) was immersed into the certain oil or water for 30 minutes to reach the equilibrium and then was drained for another 20 minutes to determine the weight. The absorption capability can be calculated by:

$$Q_r = \frac{m_x - m_d}{m_d} \quad \text{Equation (2)}$$

where $Q_r$ (g g$^{-1}$) is the absorption capability, $m_d$ (g) and $m_w$ (g) are the aerogel weight before and after the oil absorption, respectively. The error range including the standard deviation was determined by the Analysis of Variance in software "Originlab".

To determine the oil absorption kinetics, samples with identical size (cylinder shape with diameter of 6 cm and height of 3 cm) was immersed into the singer machine oil at different times to measure its weight change. The kinetic constant, $k_1$ was determined by:

$$\ln\frac{Q_m}{Q_m - Q_t} = k_1 t \quad \text{Equation (3)}$$

where $Q_m$ is the saturated absorption capacity (g g$^{-1}$), $Q_t$ is the absorption capacity (g g$^{-1}$) at time t (s).

For the distillation absorption cycling experiment, after the absorption of ethanol, aerogels were placed into a flask and heated at 100° C. with a condenser to collect the recycled ethanol. For the squeezing absorption cycling experiment, after the absorption of ethanol, the aerogel was squeezed to one fourth of the original height to release the ethanol.

Results and Discussion

Figure 9:
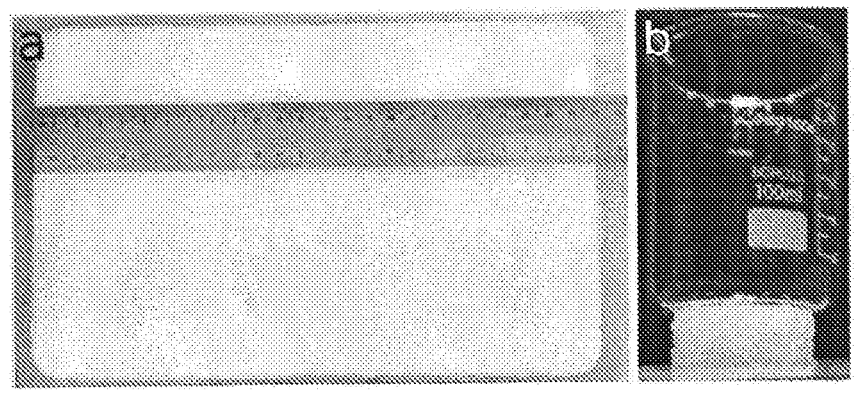
FIG. 9 shows (a) a large-scale CC1-1 aerogel, (b) a photograph of the CC1-1 aerogel withstanding weight on top of it, and (c) MTMS-coated CC1-1 aerogel which does not absorb water droplets placed on its surface.
Figure 9:
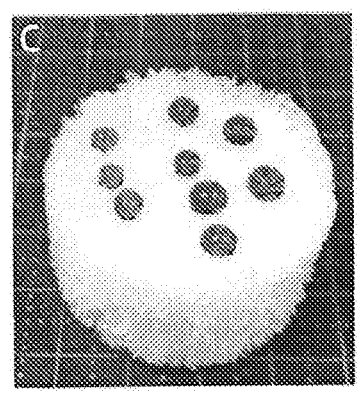

The PC and CC aerogels possess good handleability. Various shapes and sizes of the developed aerogels may be controlled by molding. FIG. 9(a) shows that a large-scale CC aerogel having 1-cm thickness, 0.50 weight % and the cotton-cellulose ratio of 1-1 can be fabricated using the A4-sized tray. The good handleability of the CC aerogel is shown with a height change of less than 80% when placed on a 100 ml glass beaker weighing ~53 g, which is nearly 100 times the weight of the aerogel (FIG. 9(b)). FIG. 9(c) shows that the MTMS-coated CC aerogel does not absorb small water droplets (dyed with blue ink) placed on its top surface, confirming its hydrophobicity.

Figure 10:
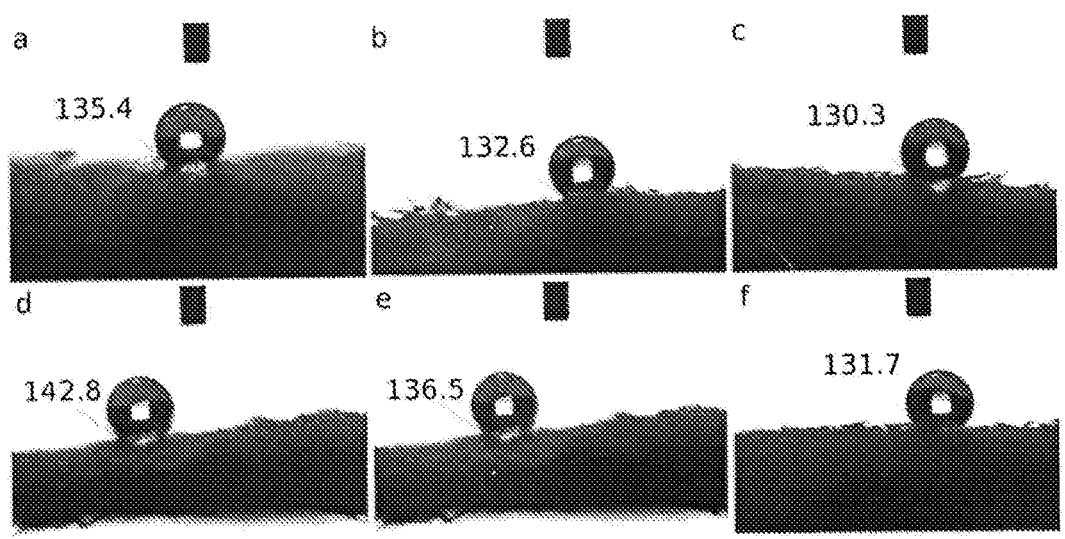
FIG. 10 shows the contact angles of the MTMS-coated PC aerogels with different concentrations: (a) PC25, (b) PC50, (c) PC75 of the cotton fibres and MTMS-coated CC aerogels having the same 0.50 weight % of the fibres with different cotton-cellulose ratios: (d) CC1-1, (e) CC1-2 and (f) CC1-4.

The results of water contact angle tests of different PC and CC aerogels are shown in FIG. 10. A large contact angle over 130° of all PC and CC aerogels indicates their hydrophobic properties. The contact angle slightly decreases with the increase of the cotton concentration. This occurs because the homogenous silanization process may be less effective. Compared with the 0.50 weight % PC aerogel, the CC aerogels with the same 0.50 weight % have a larger contact angle up to 142.8°. The higher content of cellulose fibres adds more hydroxyl groups exposed to the MTMS vapour, which are replaced by the alkoxy groups and therefore make the surface of the CC aerogel more hydrophobic. The further increase of cellulose content also brings about the decrease of the water contact angle, due to a less-efficient coating.

Figure 11:
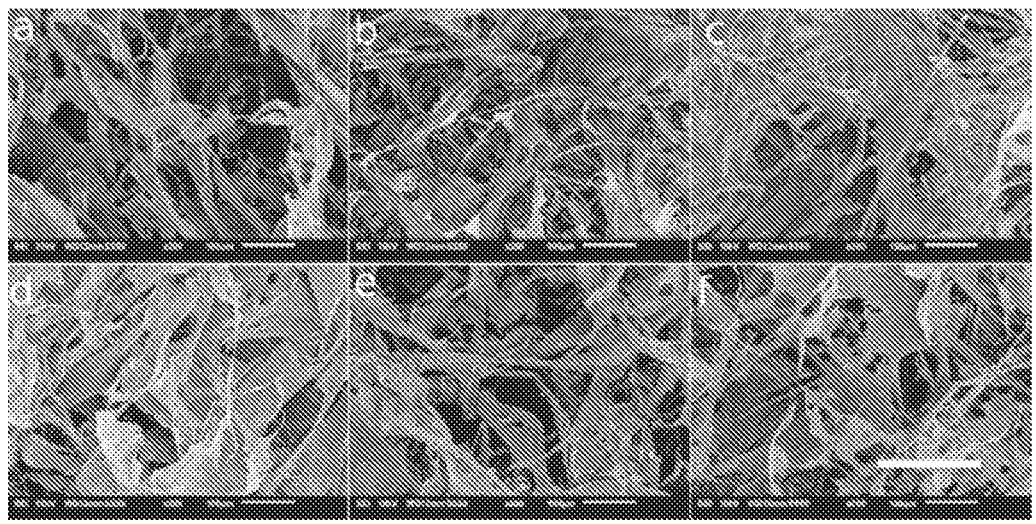
FIG. 11 shows FESEM images of the PC aerogels with different concentrations of (a) PC25, (b) PC50, (c) PC75 and the CC aerogels with different cotton-paper cellulose ratios of (d) CC1-1, (e) CC1-2, (f) CC1-4.

The PC and CC aerogels present macropores with diameters larger than 50 μm estimated from the SEM images in FIG. 11. For the PC aerogels, the increase in the cotton fibre concentration causes the formation of a more packed structure as seen in FIGS. 11(a) to (c). For the CC aerogels shown in FIGS. 11(d) to (f), the increase of the cellulose fibres also causes formation of a more packed structure. It may be explained that the cellulose fibres can be dispersed better than the cotton fibres.

Figure 12:
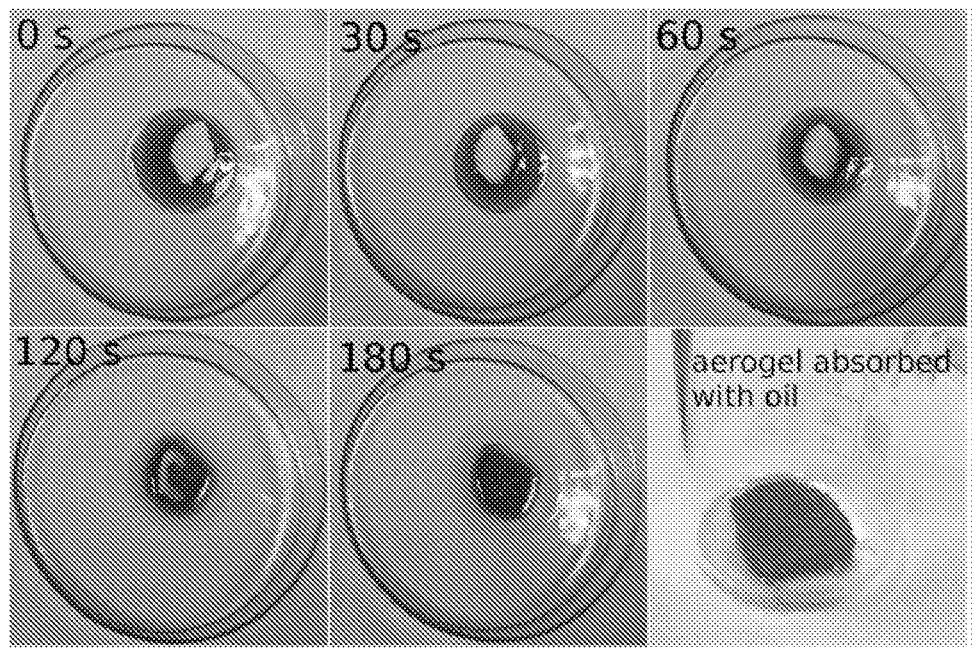
FIG. 12 shows the oil absorption process of the CC1-1 aerogel in the time indicated.

FIG. 12 demonstrates the absorption process of machine oil (dyed using Sudan Red) using the CC1-1 aerogel with a size of 2×2×0.5 cm aerogel. The aerogel initially floats on the oil and then gradually sinks down upon the absorption of the oil. The absorption is completed in 180 seconds. Besides, the CC aerogels can be shaped into small pellets to treat and remove the oil from water. The aerogel pellets are advantageous because they are able to reduce storage space in view of their size, as well as making transportation of the aerogels much easier.

Figure 13:
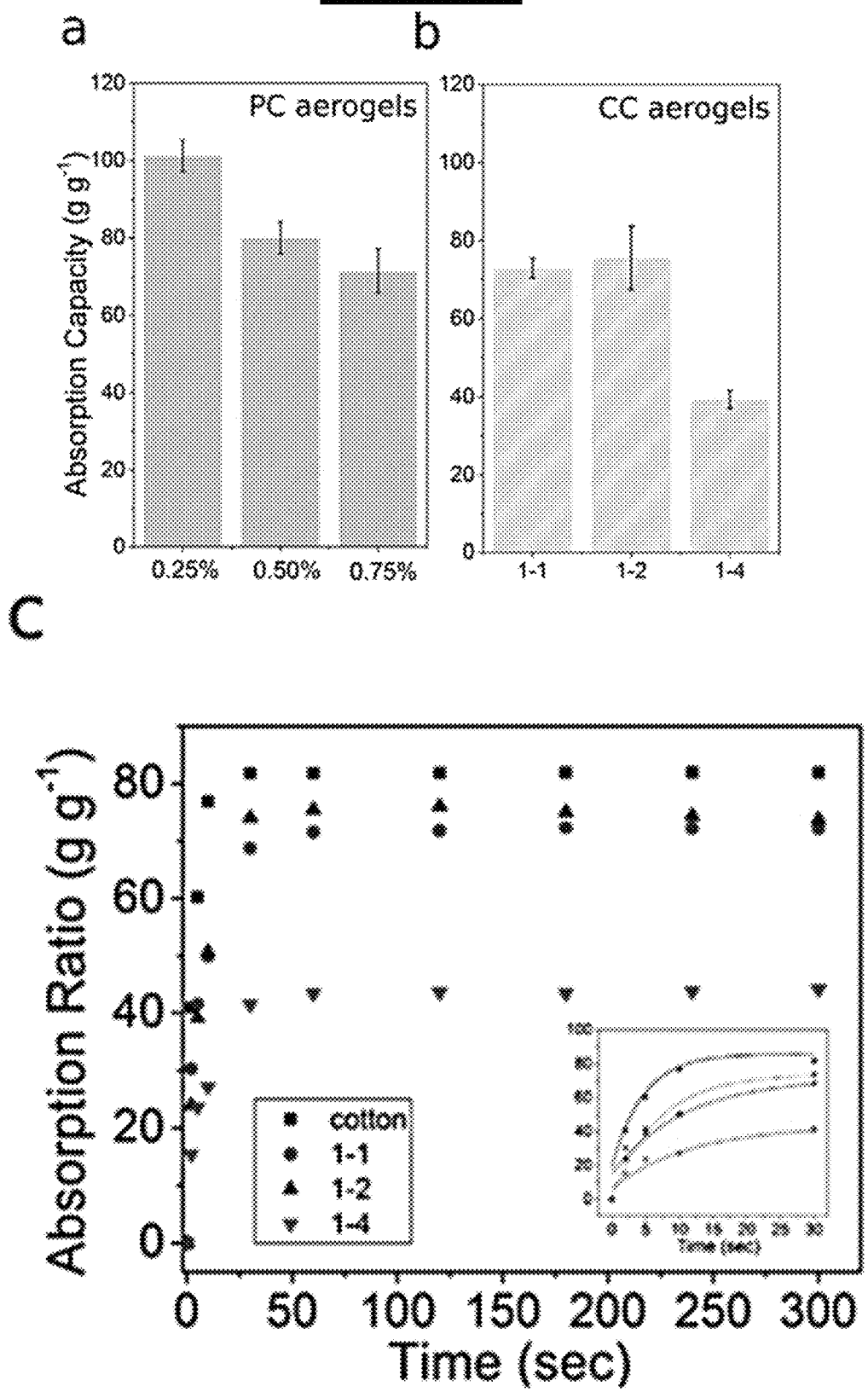
FIG. 13 shows machine oil absorption capacities of (a) the PC aerogels with different cotton fibre concentrations (0.25-0.75 weight %), (b) CC aerogels with different cotton-paper cellulose ratios (1-1 to 1-4) and (c) absorption kinetics of PC50 aerogel and CC aerogels with different cotton-paper cellulose ratios (Figure inset is the absorption result in initial 30 seconds with fitting lines)

FIG. 13 exhibits the machine oil absorption capabilities of the PC and CC aerogels. Samples with different fibre concentrations clearly show different absorption performances as analyzed by F-test using one-way Anova. As can be seen in FIG. 13($a$), the PC aerogel with a low concentration of 0.25 weight % has the highest absorption capacity over 100 g g$^{-1}$, much larger than those of the commercial sorbents. The increase in the cotton fibre concentration from 0.25 weight % to 0.75 weight % decreases the absorption capability of the PC aerogels due to their raised density and lower porosity as listed in Table 3. For the CC aerogels as shown in FIG. 13($b$), both CC1-1 and CC1-2 aerogels present competitive oil absorption compared to the PC aerogels with same fibre concentration of 0.50 wt %. It is also important to note that during the draining period to remove the oil absorbed, the CC aerogels show little shape change while the PC aerogel shrinks to 80% of its original volume. This shows that the composite aerogel has better mechanical stability compared to the pure cotton aerogel. With the further increase in the paper cellulose fibres, there is a decrease of the absorption capability despite its smaller density. This may be due to the dense structure as shown in FIG. 11($f$) which can prevent the oil diffusion and entrap the air inside the aerogels. Further, the higher the percentage of the paper cellulose fibres, there is a less effective silanization process due to more exposed hydroxy groups while the amount of MTMS used for coating is fixed.

Interestingly, it was found that although the water absorption capacity of PC aerogels is high, it is much smaller than the absorption capacity of machine oil, regardless of the larger density of the water. Both cotton aerogels and cotton-paper cellulose aerogels swelled during the water absorption tests. However only cotton aerogels swelled during the oil absorption tests. Also, it was found that during the draining process after the water absorption capability test, the prepared cotton aerogels underwent an observable shrinkage (~60% volume change) once taken out from the water. Meanwhile, this volume shrinkage is much smaller in the oil absorption tests. This may be due to the high viscosity of the machine oil compared with water. This difference, however, is much smaller in the CC aerogels, indicating their improved mechanical strength.

The absorption kinetic results are shown in the FIG. 13($c$). The PC50 aerogel has the highest absorption speed compared with the CC aerogels. But the CC1-4 aerogel has the lowest absorption capability and sluggish absorption kinetic, possibly due to its least hydrophobicity. The initial absorption kinetic constants are obtained by fitting the results according to the notable first-order pseudo equation 3. The kinetic constants of the PC50, CC1-1, CC1-2, and CC1-4 aerogels are 0.217, 0.094, 0.143 and 0.189, respectively.

Figure 14:
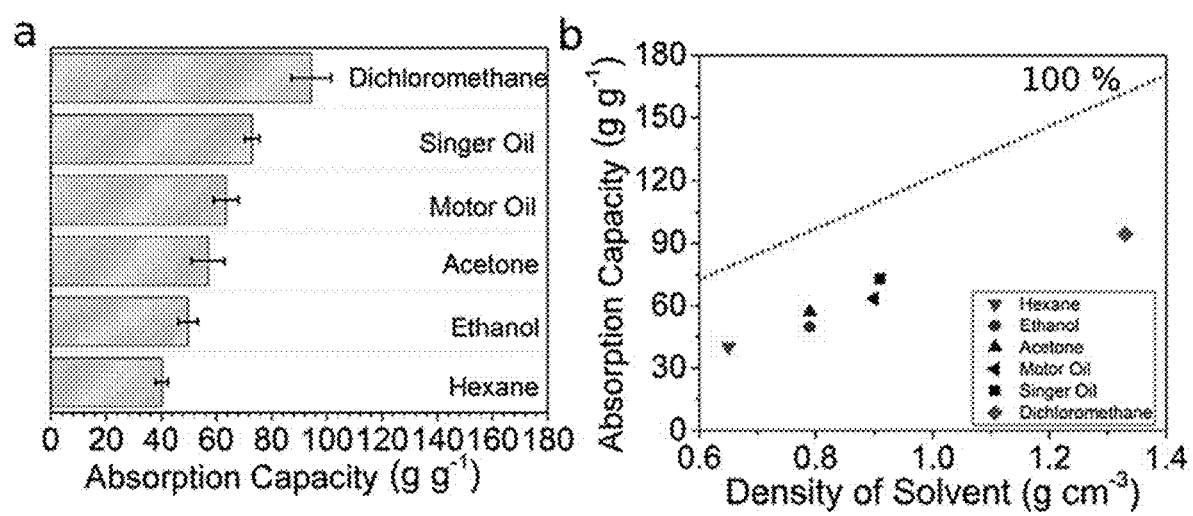
FIG. 14 shows the various solvent absorption capacity of the (a) CC1-1 aerogel and (b) absorption capacity marked with liquid density.

Besides the machine oil, the aerogels were also tested with other organic solvents. As can be seen in the FIG. 14, the CC1-1 aerogel presents the highest absorption capacity for dichloromethane and the least for hexane. Generally, the absorption capacity increases with the density of the solvent. However, the absorption capacity for the acetone is higher than that for the ethanol regardless of their close density (FIG. 14($b$)). The absorption capacities of the PC and CC aerogels were higher than those of conjugated polymers, nanowire membrane, exfoliated graphite, carbon aerogel and competitive to spongy CNT and graphene. The theoretical absorption ratio was also plotted based on the solvent density and sample porosity (porosity×$\rho_{liquid}/\rho_{aerogel}$). Current absorption capacities of the CC1-1 aerogels for the different solvents are near the line of the theoretical absorption capacity.

Figure 15:
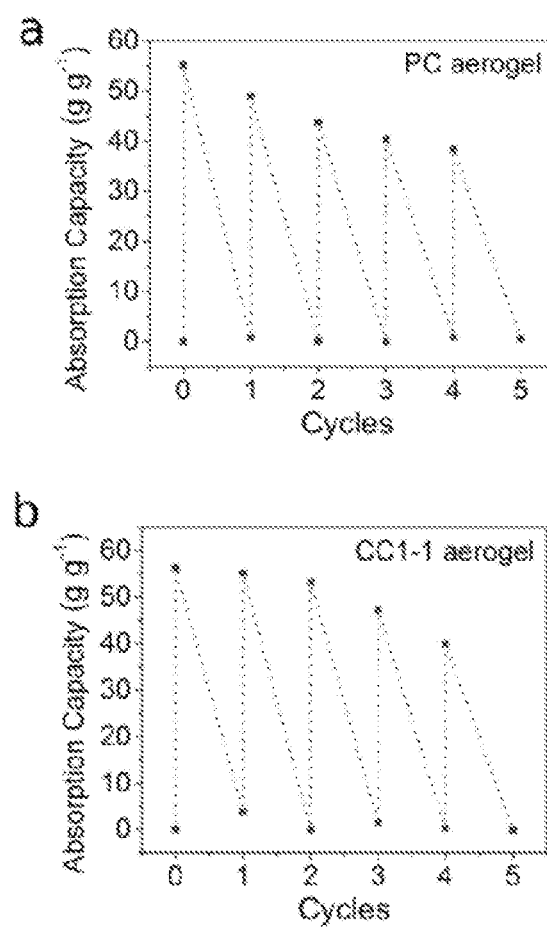
FIG. 15 shows the distillation cycling of (a) the PC50 aerogel and (b) the CC1-1 aerogel for ethanol absorption.

More importantly, the absorbed liquids may be re-collected through distillation. FIG. 15 shows the absorption-distillation cycles of the ethanol. Both PC50 and CC1-1 aerogels undergo minor shrinkage during the distillation process due to the capillary force during the liquid-vapour phase transition. After 5 cycles of liquid recovery, the PC50 and CC1-1 aerogels yield the absorption capacities of 38 ad 40 g g$^{-1}$, respectively. The CC1-1 aerogel presents a slightly better performance because the strengthening effects of two different cotton and cellulose fibres.

Conclusions

In summary, cotton-paper cellulose composite aerogels have been prepared using commercial cotton and cellulose fibres from paper waster. The functionalized aerogels with hydrophobicity demonstrate a good contaminant absorption with 72.3 g g$^{-1}$ in machine oil and 94.3 g g$^{-1}$ for dichloromethane. The cotton-paper cellulose composite aerogel presents a slightly better performance because the synergistic effects of two different cotton and cellulose fibres Whilst the foregoing description has described exemplary embodiments, it will be understood by those skilled in the technology concerned that many variations may be made without departing from the present invention.

The invention claimed is:

1. A polysaccharide aerogel, comprising cotton cellulose fibres and paper cellulose fibres, wherein the cotton cellulose fibres and the paper cellulose fibres are comprised in the aerogel in a weight ratio of 1:1 to 1:6.

2. The aerogel of claim 1, wherein the aerogel is compressible.

3. The aerogel of claim 1, wherein the aerogel is formed from a hydrogel comprising 0.5-1.5 weight % cotton cellulose fibres.

4. The aerogel of claim 1, wherein the aerogel further comprises at least one additive.

5. The aerogel of claim 4, wherein the at least one additive comprises chitosan.

6. The aerogel of claim 1, wherein the aerogel comprises at least one cross-linker.

7. The aerogel of claim 6, wherein the at least one cross-linker comprises a wet-strength resin.

8. A device, comprising the aerogel of claim 1.

9. A method of forming the aerogel of claim 1, the method comprising:
   mixing cotton cellulose fibres and paper cellulose fibres in a weight ratio of 1:1 to 1:6 and a cross-linker to form a mixture;
   sonicating the mixture;
   freezing the sonicated mixture; and
   freeze drying the frozen mixture to form the aerogel.

10. The method of claim 9, wherein the mixing further comprises mixing at least one additive.

11. The method of claim 10, wherein the at least one additive is chitosan.

12. The method of claim 9, wherein the method further comprises compressing the aerogel following the freeze drying.

\* \* \* \* \*